(12) United States Patent
Reuter et al.

(10) Patent No.: US 7,754,908 B2
(45) Date of Patent: Jul. 13, 2010

(54) TUNGSTEN AND MOLYBDENUM COMPOUNDS AND THEIR USE FOR CHEMICAL VAPOUR DEPOSITION (CVD)

(75) Inventors: Knud Reuter, Krefeld (DE); Jörg Sundermeyer, Marburg (DE); Alexei Merkoulov, Moskau (RU); Wolfgang Stolz, Marburg (DE); Kestin Volz, Dautphetal (DE); Michael Pokoj, Fernwald (DE); Thomas Ochs, Kirchheim-Betziesdorf (DE)

(73) Assignee: H. C. Starck Clevios GmbH, Goslar (DE)

( * ) Notice: Subject to any disclaimer, the term of this patent is extended or adjusted under 35 U.S.C. 154(b) by 371 days.

(21) Appl. No.: 11/649,504

(22) Filed: Jan. 4, 2007

(65) Prior Publication Data
US 2007/0160761 A1    Jul. 12, 2007

(30) Foreign Application Priority Data
Jan. 5, 2006    (DE) .................. 10 2006 000 823

(51) Int. Cl.
*C07F 11/00*    (2006.01)
(52) U.S. Cl. ........................................ 556/57

(58) Field of Classification Search .................. 556/57
See application file for complete search history.

(56) References Cited

FOREIGN PATENT DOCUMENTS

| WO | WO-2004/007796 A1 | 1/2004 |
| WO | WO 2004/007796 A1 * | 1/2004 |

* cited by examiner

*Primary Examiner*—Joseph R Kosack
(74) *Attorney, Agent, or Firm*—Connolly Bove Lodge & Hutz LLP

(57) ABSTRACT

The present invention relates to specific novel tungsten and molybdenum compounds

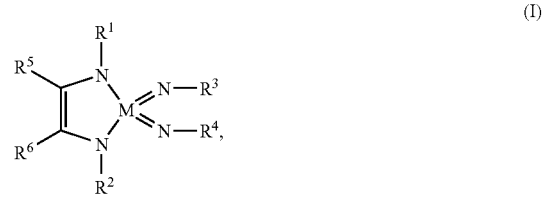

(I)

to the use thereof for the deposition of tungsten- or molybdenum-containing layers by means of chemical vapour deposition, and to the tungsten- or molybdenum-containing layers produced by this process.

8 Claims, No Drawings

TUNGSTEN AND MOLYBDENUM COMPOUNDS AND THEIR USE FOR CHEMICAL VAPOUR DEPOSITION (CVD)

The present invention relates to specific novel tungsten and molybdenum compounds, to the use thereof for the deposition of tungsten- or molybdenum-containing layers by means of chemical vapour deposition, and to the tungsten- or molybdenum-containing layers produced by this process.

Tungsten nitride is a highly promising material for barrier layers in integrated circuits with copper conductors, for example because of its resistivity and its excellent thermal, chemical and mechanical resistance. Its electrical conductivity is high, and it does not form mixed phases with copper. Such W—N-based layers for use in Si microelectronics can at present be produced by plasma-based deposition processes (physical vapour deposition, PVD). However, in view of the extremely high demands that are being made of ever more highly integrated circuits, for example conformal layer deposition on structured surfaces ("step coverage"), PVD processes come up against the limits of technical feasibility. For such applications, use is increasingly being made of chemical gas-phase deposition (chemical vapour deposition, CVD) to atomic-layer-accurate deposition using a specific CVD process, so-called atomic layer deposition (ALD). For such CVD processes it is, of course, necessary for corresponding chemical starting materials of the individual elements to be available for the desired layers.

At the present time there are used for the CVD of W-based layer structures predominantly halides, such as, for example, $WF_6$ or $WCl_6$, see, for example, B. J. P. Lu, W. Y. Hsu, J. D. Luttmer, L. K. Magel and H. L. Tsai, *J. Electrochem. Soc.* 145 (1998), L21-L23, or A. E. Kaloyeros and E. Eisenbraun, *Annu. Rev. Mater. Sci.* 30 (2000), 363-385. This is associated with various disadvantages. On the one hand, halogen radicals are in many cases undesirable for the construction of complex layer structures on account of their caustic/corrosive properties, and on the other hand tungsten fluoride has disadvantages owing to its low volatility and its high deposition temperature. Tungsten(VI) amide imides, such as, for example, ($^tBuN=$)$_2$W(NH$^tBu$)$_2$ (see H. T. Chiu and S. H. Chuang, *J. Mater. Res.* 8 (1993), 1353) or ($^tBuN=$)$_2$W(NMe)$_2$ (see J. S. Becker, S. Suh, S. Wang and R. G. Gordon, *Chem. Mater.* 15 (2003), 2969-2976), are likewise proposed. The films produced using these starting materials very often contain high, undesirable concentrations of carbon and exhibit relatively low conductivity.

Accordingly, there is a considerable need for further novel precursors, in particular for WN layers, which do not exhibit the above-mentioned disadvantages or at least bring about marked improvements compared with the known precursors.

The object underlying the present invention was, therefore, to provide such precursors.

Surprisingly, it has now been found that complex tungsten amides having a DAD ligand meet these requirements. DAD stands for radicals having the general structure (A) derived from 1,4diaza-butadiene

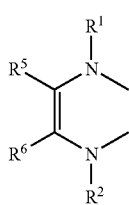

(A)

wherein
R$^1$ and R$^2$ independently of one another represent optionally substituted C$_1$- to C$_{12}$-alkyl, C$_5$- to C$_{12}$-cycloalkyl, C$_6$- to C$_{10}$-aryl radicals, 1-alkenyl, 2-alkenyl, 3-alkenyl radicals, triorganosilyl radicals —SiR$_3$ or amino radicals NR$_2$, wherein R represents a C$_1$- to C$_4$-alkyl radical,
R$^5$ and R$^6$ independently of one another represent H, optionally substituted C$_1$- to C$_{12}$-alkyl, C$_5$- to C$_{12}$-cycloalkyl or C$_6$- to C$_{10}$-aryl radicals.

The invention relates further to the analogous molybdenum compounds. These are suitable, for example, as CVD precursors for conductive molybdenum nitride layers (MoN).

The invention therefore provides compounds of the general formula (I)

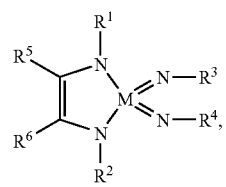

(I)

wherein
M represents Mo or W,
R$^1$ and R$^2$ independently of one another represent an optionally substituted C$_1$- to C$_{12}$-alkyl, C$_5$- to C$_{12}$-cycloalkyl, C$_6$- to C$_{10}$-aryl radical, a 1-alkenyl, 2-alkenyl, 3-alkenyl radical, a triorganosilyl radical —SiR$_3$ or an amino radical NR$_2$, wherein R represents a C$_1$- to C$_4$-alkyl radical,
R$^3$ and R$^4$ independently of one another represent an optionally substituted C$_1$- to C$_8$-alkyl, C$_5$- to C$_{10}$-cycloalkyl, C$_6$- to C$_{14}$-aryl radical, SiR$_3$ or NR$_2$, wherein R is as defined hereinbefore, and
R$^5$ and R$^6$ independently of one another represent H or an optionally substituted C$_1$- to C$_{12}$-alkyl, C$_5$- to C$_{12}$-cycloalkyl or C$_6$- to C$_{10}$-aryl radical.

Unless indicated otherwise, substituted is here understood as meaning substitution by C$_1$- to C$_4$-alkoxy or di(C$_1$- to C$_4$-alkyl)amino radicals.

Preferred compounds of the general formula (I) according to the invention are tungsten and molybdenum compounds of the general formula (II)

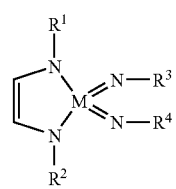

(II)

wherein
M represents W or Mo,
R$^1$ and R$^2$ represent identical C$_1$- to C$_5$-alkyl or C$_5$- to C$_6$-cycloalkyl radicals, and
R$^3$ and R$^4$ independently of one another represent a C$_1$- to C$_5$-alkyl radical, a C$_5$- to C$_6$-cycloalkyl radical, a C$_6$- to C$_{10}$-aryl radical optionally substituted by from one to three C$_1$- to C$_5$-alkyl groups—preferably an optionally substituted phenyl radical —SiR$_3$ or NR$_2$, wherein R represents C$_1$-C$_4$-alkyl.

These are particularly preferably tungsten and molybdenum compounds having tert-butyl-substituted DAD ligands, which have the structure (III):

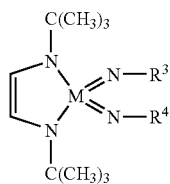

(III)

wherein
$R^3$ and $R^4$ independently of one another represent a radical from the group of the $C_1$- to $C_5$-alkyl radicals, $C_6$- to $C_{10}$-aryl radicals optionally substituted by from one to three $C_1$- to $C_5$-alkyl groups—preferably optionally substituted phenyl radicals —$SiR_3$ or $NR_2$.

These are very particularly preferably compounds having the structure (IV)

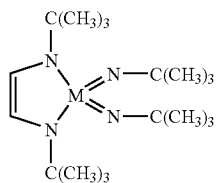

(IV)

wherein M represents W or Mo.

Alkyl or alkoxy, each independently of the other, represents a straight-chained, cyclic or branched alkyl or alkoxy radical, wherein the mentioned radicals can optionally further be substituted. The same applies to the alkyl moiety of a trialkylsilyl or mono- or di-alkylamino radical or to the alkyl moiety of mono- or di-alkylhydrazines or mono-, di-, tri- or tetra-alkylsilanes.

Within the scope of the invention, $C_1$-$C_4$-alkyl represents, for example, methyl, ethyl, n-propyl, isopropyl, n-butyl, sec-butyl, tert-butyl, $C_1$-$C_5$-alkyl additionally represents, for example, n-pentyl, 1-methylbutyl, 2-methylbutyl, 3-methylbutyl, neopentyl, 1-ethylpropyl, 1,1-dimethylpropyl, 1,2-dimethylpropyl, 1,2-dimethylpropyl, $C_1$-$C_6$-alkyl additionally represents, for example, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, $C_1$-$C_{12}$-alkyl additionally represents, for example, n-heptyl and n-octyl, n-nonyl, n-decyl and n-dodecyl.

1-Alkenyl, 2-alkenyl, 3-alkenyl represent, for example, the alkenyl groups corresponding to the above alkyl groups. $C_1$-$C_4$-Alkoxy represents, for example, the alkoxy groups corresponding to the above alkyl groups, such as, for example, methoxy, ethoxy, n-propoxy, isopropoxy, n-butoxy, sec-butoxy, tert-butoxy.

$C_5$-$C_{12}$-Cycloalkyl represents, for example, optionally substituted mono-, bi- or tri-cyclic alkyl radicals. Examples are cyclopentyl, cyclohexyl, cycloheptyl, pinanyl, adaman-tyl, the isomers of menthyl, n-nonyl, n-decyl, n-dodecyl. Preferred as $C_5$-$C_6$-cycloalkyl are cyclopentyl and cyclohexyl.

Aryl, in each case independently, represents an aromatic radical having from 6 to 14, preferably from 6 to 10, skeletal carbon atoms, in which none, one, two or three skeletal carbon atoms per ring can be substituted by hetero atoms selected from the group nitrogen, sulfur and oxygen, but preferably represents a carbocyclic aromatic radical having from 6 to 14, preferably from 6 to 10, skeletal carbon atoms.

Examples of optionally substituted $C_6$-$C_{10}$-aryl are phenyl, 2,6-diisopropylphenyl, o-, p-, m-tolyl or naphthyl.

The carbocyclic aromatic radical or heteroaromatic radical can furthermore be substituted by up to five identical or different substituents per ring, the substituents being selected from the group fluorine, cyano, $C_1$-$C_{12}$-alkyl, $C_1$-$C_{12}$-fluoroalkyl, $C_1$-$C_{12}$-fluoroalkoxy, $C_1$-$C_{12}$-alkoxy and di($C_1$-$C_8$-alkyl)amino.

The compounds according to the invention can be prepared in a simple manner, by reacting DAD ligand precursors of the general formula (B)

(B)

wherein $R^1$, $R^2$, $R^5$ and $R^6$ are as defined hereinbefore, in the presence of at least one reducing agent, with Mo or W complexes of the general formula (C)

[$M(NR^3)(NR^4)Cl_2L_2$]

wherein
M represents W or Mo,
L represents a ligand selected from aliphatic or aromatic amines, ethers, halide, preferably chloride, and nitriles, preferably acetonitrile,
$R^3$ and $R^4$ are as defined hereinbefore,
in a suitable solvent, preferably at a temperature of from −20° C. to 120° C.

Suitable reducing agents are base metals such as, for example, Mg, Zn, Li, Na, Al, etc. Examples of suitable solvents are ethers, for example THF, diethyl ether or 1,2-dimethoxyethane, dipolar aprotic solvents, for example acetonitrile, N,N-dimethylformamide or tertiary amines, or aliphatic or aromatic hydrocarbons, for example toluene, pentane, hexane, etc., as well as mixtures thereof. The Mo or W complexes of the general formula (C) [$M(NR^3)(NR^4)Cl_2L_2$] can be prepared in isolated form or in situ according to generally known processes.

In addition, it is also possible to reduce the DAD ligand precursor of the general formula (B) with the reducing agent beforehand in a suitable solvent, so that solutions of the pre-reduced DAD ligands, such as, for example when using Li as reducing agent, Li[DAD] or Li$_2$[DAD], are reacted with the solution of the complexes of the general formula (C). By carefully selecting and controlling the reaction temperature at from −20° C. to 120° C. it is also possible to prepare the compounds according to the invention in a one-pot synthesis, in which WCl$_6$, for example, is combined with the amine(s)

$H_2NR^3$ or $H_2NR^4$, the reducing agent and the DAD ligand precursor of the general formula (B) and reacted.

For isolation of the compounds according to the invention, the solvent is removed, for example by means of distillation under reduced pressure, which can be followed by further purification by means of washing as well as by subsequent drying. Such suitable processes are known to the person skilled in the art.

From the tungsten and molybdenum compounds according to the invention there can be produced tungsten- and/or molybdenum-containing metals, metal alloys, oxides, nitrides and carbides, as well as mixtures thereof and/or compounds in amorphous and/or crystalline form, by means of CVD, ALD (atomic layer deposition) and thermal decomposition. Such mixtures and compounds are used, for example, as dielectric layers in capacitors and gates in transistors, microwave ceramics, piezo ceramics, thermal and chemical barrier layers, diffusion barrier layers, hard material coatings, electrically conductive layers, anti-reflection layers, optical layers and layers for IR mirrors. The tungsten and molybdenum compounds according to the invention are also suitable as precursors for flame pyrolyses for the production of powders.

The invention accordingly relates also to the use of the tungsten and molybdenum compounds according to the invention for the deposition of tungsten- and/or molybdenum-containing layers, optionally with the admixture of further compounds for the defined establishment of specific concentrations of the respective elements in the layer by means of chemical vapour deposition (CVD).

Preference is given to the use of the compounds according to the invention as precursors for tungsten nitride (WN) layers or molybdenum nitride layers by means of CVD.

The invention further provides the tungsten- or molybdenum-containing layers, preferably WN or MoN layers, correspondingly produced from the compounds according to the invention by means of CVD.

The invention further provides substrates having one or more such tungsten- or molybdenum-containing layers according to the invention, preferably WN or MoN layers. Such substrates can be, for example, silicon wafers or silicon wafers already provided with further surface-structured single or multiple layers, as are typically used in the production of Si-based integrated circuits. Accordingly, substrates within the scope of the invention can also be, for example, surfaces of metals or dielectrics.

The compounds according to the invention are preferably used in a CVD process comprising the following process steps:

A suitable substrate, for example a Si wafer or alternatively a Si wafer already provided with further surface-structured single or multiple layers, as are typically used in the production of Si-based integrated circuits, is introduced into a CVD unit and heated to a temperature suitable for layer deposition in the range of from 250° C. to 700° C. A carrier gas is loaded with the starting materials in defined concentrations, it being possible for inert gases, for example $N_2$ and/or Ar, also in combination with inert, vaporised solvents, for example hexane, heptane, octane, toluene or butyl acetate, to be used as the carrier gas, and also for reactive, e.g. reducing, gases, such as, for example, $H_2$, to be added. The loaded carrier gas is passed over the surface of the heated substrate for a defined exposure time, the respective concentrations of starting materials and the exposure time being matched to one another with the proviso that a W— or Mo-containing layer having a predetermined layer thickness and a predetermined composition is formed on the surface of the substrate, in either amorphous, nano- or micro-crystalline or polycrystalline form. Typical exposure times are, for example, from a few seconds to several minutes or hours, depending on the deposition rate. Typical deposition rates can be, for example, from 0.1 nm/sec to 1 nm/sec. However, other deposition rates are also possible. Typical layer thicknesses are, for example, from 0.1 to 100 nm, preferably from 0.5 to 50 nm, particularly preferably from 1 to 10 nm.

Within the scope of CVD technology it is advantageous to use, in addition to the starting materials according to the general formula (I), preferably of the general formulae (II) to (IV), for the preparation of pure W or Mo metal layers, W— or Mo-rich layers as well as W—N— or Mo—N-containing mixed layers, also the following starting materials for specifically establishing the nitrogen concentration (N concentration) of W—N— or Mo—N-containing mixed system layers—also referred to as N starting materials hereinbelow:

ammonia ($NH_3$), mono($C_1$-$C_{12}$-alkyl)hydrazines, in particular tert-butylhydrazine ($^tBu$—NH—$NH_2$), and/or 1,1-di($C_1$-$C_5$-alkyl)hydrazines, in particular 1,1-dimethylhydrazine (($CH_3$)$_2$N—$NH_2$). It can be beneficial, in particular in order to influence the stability of the prepared mixed system layers in subsequent high-temperature heating steps, to add further elements in the CVD deposition, in order to influence the recrystallisation behaviour of the resulting layer. The element silicon (Si) is particularly suitable for use in Si-based integrated circuits. For the preparation of W—N—Si— or Mo—N—Si-containing mixed system layers there are advantageously used in CVD technology, in addition to the starting materials mentioned above, the following starting materials for adjusting the silicon concentration—also referred to as Si starting materials hereinbelow:

silane ($SiH_4$), disilane ($Si_2H_6$), mono($C_1$-$C_{12}$-alkyl)silanes, in particular tert-butylsilane ($^tBu$—$SiH_3$), di($C_1$-$C_{12}$-alkyl)silanes, in particular di-tert-butylsilane ($^tBu_2SiH_2$), tri($C_1$-$C_{12}$-alkyl)silanes, in particular triethylsilane (($C_2H_5$)$_3$SiH), and/or tetra($C_1$-$C_{12}$-alkyl)silanes, in particular tetraethylsilane (($C_2H_5$)$_4$Si).

When carrying out the process according to the invention, the precise concentrations of the starting materials are governed in principle by the thermal decomposition properties of the respective starting materials in the CVD process. The starting materials are preferably used in the following molar ratios: N starting material(s)/W or Mo compound according to the invention in ratios of from 0:1 to 20,000:1 and Si starting material(s)/W or Mo starting material according to the invention in ratios of from 0:1 to 100:1. The surface temperature of the substrate is preferably adjusted to temperatures in the range of from 300° C. to 600° C. The overall pressure of carrier gas and starting materials is preferably adjusted to pressures in the range of from 10 hPa to 1000 hPa, the ratio of the partial pressure of the sum of all starting materials to the partial pressure of the carrier gas being preferably from 0.0001 to 0.5. The deposition rate is preferably from 0.05 nm/min to 50 nm/min.

The following points are to be regarded as technical advantages of the present invention:
1) The synthesis of the volatile tungsten and molybdenum compounds does not require expensive lithium alkyls or amides.
2) The introduction of the DAD ligand as the CVD-suitable leaving group for W(III) or Mo(III) layers reduces the risk of the undesirable incorporation of carbon into the substrate coating.
3) In the combination with N starting materials, for example with hydrazine 25 derivatives (e.g. 1,1-dimethylhydrazine or tert-butylhydrazine), a specific change in the layer composition in the CVD is possible.

The Examples which follow serve to explain the invention by way of example and are not to be interpreted as limiting.

EXAMPLES

In the Examples which follow, the abbreviations and abbreviated compound names denote the following structures:

D$^t$BuAD=1,4-di-tert-butyl-1,4-diaza-butadiene or its divalent radical=

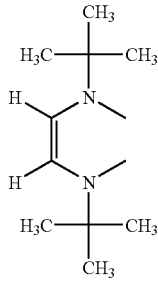

$^t$Bu=tert-butyl
$^t$BuN=$^t$Bu-N=tert-butylimino
Py=pyridine
DME=dimethoxyethane

Example 1

Preparation of (D$^t$BuAD)Mo(N$^t$Bu)$_2$ 1.69 g of D$^t$BuAD (10.0 mmol) and 0.24 g of Mg powder (10.0 mmol) are added to a solution of 4.00 g of Mo(N$^t$Bu)$_2$Cl$_2$(dme) (10.0 mmol) in 50 ml of THF at 0° C. The reaction mixture is stirred for one day at 23° C. The solvent is then removed at 20 mbar and the product is extracted twice using 100 ml of hexane each time. The hexane is then evaporated off and the residue sublimes at 90° C./10$^{-2}$ mbar. Yield: 2.44 g (60 %), orange-coloured solid; m.p. 79° C.

Elemental analysis for $C_{18}H_{38}N_4Mo$ (M=406.47 g·mol$^{-1}$): calc. (%) C, 53.19; H, 9.42; N, 13.78; found (%) C, 52.62; H, 9.35; N, 13.65.

MS-EI: 408 (M$^+$, 41%), 393 (M$^+$-Me, 100%), 352 (M$^+$-Me$_2$C=CH$_2$, 3%), 337 (M$^+$-Me-Me$_2$C=CH$_2$, 23%), 296 (M$^+$-2 Me$_2$C=CH$_2$, 3%), 281 (M$^+$-Me-2 Me$_2$C=CH$_2$, 6%).

$^1$H-NMR (C$_6$D$_6$, 300 MHz, 300 K): 6.05 (s, 2H, CH-DAD), 1.56 (s, 9H, N$^t$Bu), 1.33 (s, 18H, $^t$Bu-DAD), 1.26 (s, 9H, N$^t$Bu).

$^{13}$C{$^1$H}-NMR (C$_6$D$_6$, 75 MHz, 300 K); 113.4 (CH-DAD), 66.7 and 65.9 (NC(CH$_3$)$_3$), 55.9 (C(CH$_3$)$_3$-DAD), 33.6 and 33.1 (NC(CH$_3$)$_3$), 32.0 (C(CH$_3$)$_3$-DAD).

IR (KBr, cm$^{-1}$): 3182 (w), 3010 (w), 1414 (w), 1361 (s), 1262 (w), 1246 (m), 1217 (s), 1120 (w), 1055 (w), 1021 (w), 936 (w), 875 (w), 814 (w), 805 (w), 773 (w), 724 (w), 673 (w), 638 (w), 605 (w), 581 (w), 551 (w), 518 (w), 470 (w).

Example 2

Preparation of (D$^t$BuAD)W(N$^t$Bu)$_2$ 610 mg of D$^t$BuAD (3.6 mmol) and 90 mg of Mg powder (3.7 mmol) are added to a solution of 2.00 g of W(N$^t$Bu)$_2$Cl$_2$Py$_2$ (3.6 mmol) in 50 ml of THF at 0° C. The reaction mixture is stirred for one day at room temperature. The solvent is removed at 20 mbar and the product is extracted twice using 100 ml of hexane each time. The hexane is then evaporated off and the residue sublimes at 100° C./10$^{-2}$ mbar. Yield: 590 mg (28%), orange-yellow solid; m.p. 73.5° C.

Elemental analysis for $C_{18}H_{38}N_4W$ (M=494.38 g·mol$^{-1}$): calc. (%) C, 43.73; H, 7.75; N, 11.33; found (%) C, 43.19; H, 7.72; N, 11.27.

MS-EI: 494 (M$^+$, 28%), 479 (M$^+$-Me, 100%), 438 (M$^+$-Me$_2$C=CH$_2$, 5%), 423 (M$^+$-Me-Me$_2$C=CH$_2$, 9%), 367 (M$^+$-Me-2 Me$_2$C=CH$_2$, 3%), 311 (M$^+$-Me-3 Me$_2$C=CH$_2$, 4%)

$^1$H-NMR (C$_6$D$_6$, 300 MHz, 300 K): 6.27 (s, 2H, CH-DAD), 1.89 (s, 9H, N$^t$Bu), 1.64 (s, 18H, $^t$Bu-DAD), 1.62 (s, 9H, N$^t$Bu).

$^{13}$C{$^1$H}-NMR (C$_6$D$_6$, 75 MHz, 300 K); 109.2 (CH-DAD), 65.4 and 65.3 (NC(CH$_3$)$_3$), 56.3 (C(CH$_3$)$_3$-DAD), 34.3 and 34.1 (NC(CH$_3$)$_3$), 32.0 (C(CH$_3$)$_3$-DAD).

IR (KBr, cm$^{-1}$): 3026 (w), 1489 (w), 1402 (w), 1364 (m), 1354 (w), 1294 (m), 1248 (s), 1219 (s), 1163 (w), 1144 (w), 1113 (w), 1067 (w), 1026 (w), 972 (w), 872 (m), 814 (w), 808 (w), 774 (m), 721 (w), 660 (w), 598 (w), 673 (w), 544 (w), 519 (w), 476 (w).

The invention claimed is:

1. A compound of the general formula (III)

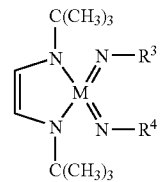

(III)

wherein
M represents W or Mo,
R$^3$ and R$^4$ independently of one another represent an optionally substituted C$_1$- to C$_8$-alkyl, C$_5$- to C$_{10}$-cycloalkyl, C$_6$- to C$_{14}$-aryl radical, SiR$_3$ or NR$_2$, wherein R represents a C$_1$- to C$_4$-alkyl radical.

2. The compound according to claim 1 wherein the compound is of the general formula (IV)

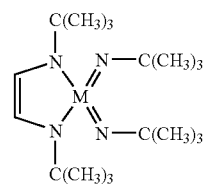

(IV)

wherein M is as defined in claim 1.
3. The compound according to claim 2, wherein M is W.
4. The compound according to claim 2, wherein M is Mo.
5. A substrate which comprises the compound of claim 1.
6. A substrate which comprises the compound of claim 2.
7. A substrate which comprises the compound of claim 3.
8. A substrate which comprises the compound of claim 4.

* * * * *